(12) United States Patent
Olson

(10) Patent No.: US 8,840,836 B2
(45) Date of Patent: Sep. 23, 2014

(54) STERILIZATION METHOD WITH COMPRESSION AND EXPANSION

(75) Inventor: Steven J. Olson, Mahtomedi, MN (US)

(73) Assignee: Sterilucent, Inc., Minneapolis, MN (US)

( * ) Notice: Subject to any disclaimer, the term of this patent is extended or adjusted under 35 U.S.C. 154(b) by 39 days.

(21) Appl. No.: 13/421,971

(22) Filed: Mar. 16, 2012

(65) Prior Publication Data

US 2012/0275954 A1 Nov. 1, 2012

Related U.S. Application Data

(60) Provisional application No. 61/479,422, filed on Apr. 27, 2011.

(51) Int. Cl.
*A61L 2/20* (2006.01)

(52) U.S. Cl.
CPC ........... *A61L 2/208* (2013.01); *A61L 2202/122* (2013.01)
USPC .......................................................... 422/33

(58) Field of Classification Search
USPC ............................................. 422/28, 33, 292
See application file for complete search history.

(56) References Cited

U.S. PATENT DOCUMENTS

| | | |
|---|---|---|
| 4,157,092 A | 6/1979 | Fare et al. |
| 4,239,731 A | 12/1980 | Gillis et al. |
| 4,512,951 A | 4/1985 | Koubek |
| 4,583,301 A | 4/1986 | Crowley et al. |
| 4,943,414 A | 7/1990 | Jacobs et al. |
| 4,952,370 A | 8/1990 | Cummings et al. |
| 4,956,145 A | 9/1990 | Cummings et al. |
| 5,492,672 A | 2/1996 | Childers et al. |
| 5,527,508 A | 6/1996 | Childers et al. |
| 5,534,221 A | 7/1996 | Hillebrenner et al. |
| 5,580,530 A | 12/1996 | Kowatsch et al. |
| 5,666,878 A * | 9/1997 | Taricco ............................ 100/73 |
| 5,851,485 A | 12/1998 | Lin et al. |
| 5,869,000 A | 2/1999 | DeCato |
| 6,010,662 A | 1/2000 | Lin et al. |
| 6,062,430 A | 5/2000 | Fuchs |
| 6,062,437 A | 5/2000 | Mascitelli |
| 6,066,294 A | 5/2000 | Lin et al. |
| 6,162,395 A | 12/2000 | Kowanko |
| 6,325,972 B1 | 12/2001 | Jacobs et al. |
| 6,451,254 B1 | 9/2002 | Wang et al. |
| 6,451,255 B1 | 9/2002 | Williams et al. |
| 6,539,975 B2 | 4/2003 | Hedenberg |
| 6,627,150 B1 | 9/2003 | Wang et al. |
| 6,656,426 B1 | 12/2003 | Wang et al. |

(Continued)

FOREIGN PATENT DOCUMENTS

| | | | | |
|---|---|---|---|---|
| EP | 0015328 | * | 9/1980 | ................ A61L 2/24 |
| GB | 1513266 | * | 11/1975 | ................ A61L 3/00 |
| WO | WO9715333 | | 5/1997 | |
| WO | WO 2004/103861 | * | 12/2004 | ................ B65F 1/14 |

*Primary Examiner* — Sean E Conley
*Assistant Examiner* — Donald Spamer
(74) *Attorney, Agent, or Firm* — Thomas J. Nikolai; Nikolai & Mersereau, P.A.

(57) ABSTRACT

An apparatus and method for achieving low temperature vapor sterilization of objects which may involve objects having a lumen. Following evacuation of the sterilization chamber and the introduction of a vaporous or gaseous sterilant, the volume of the chamber is changed by actuation of a movable boundary in the chamber to increase and decrease the pressure in the chamber thus driving the sterilant into and out of such lumens.

9 Claims, 7 Drawing Sheets

(56) References Cited

U.S. PATENT DOCUMENTS

| | | |
|---|---|---|
| 6,673,313 B2 | 1/2004 | Wang et al. |
| 6,772,794 B2 | 8/2004 | Seguin |
| 6,800,114 B2 | 10/2004 | Vanderhoof et al. |
| 6,852,279 B2 | 2/2005 | Williams et al. |
| 6,981,523 B2 | 1/2006 | Seguin |
| 7,201,869 B2 | 4/2007 | Williams et al. |
| 7,252,800 B2 | 8/2007 | Jacobs et al. |
| 7,267,806 B2 | 9/2007 | Kendall et al. |
| 7,300,638 B2 | 11/2007 | Williams et al. |
| 7,824,519 B2 | 11/2010 | Wang et al. |
| 2001/0036422 A1 | 11/2001 | Lin et al. |
| 2002/0068012 A1* | 6/2002 | Platt et al. ............... 422/22 |
| 2005/0005785 A1* | 1/2005 | Poss et al. ............... 100/240 |

* cited by examiner

STERILIZATION METHOD WITH COMPRESSION AND EXPANSION

CROSS REFERENCE TO RELATED APPLICATION

This application is a non-provisional application for Application No. 61/479,422, filed Apr. 27, 2011 and claims priority from that application which is also deemed incorporated by reference in its entirety in this application.

BACKGROUND OF THE INVENTION

II. Field of the Invention

The present invention relates to sterilization and disinfection systems that utilize gas or vapor phase sterilants or disinfectants and, more particularly, to low-temperature, hydrogen peroxide vapor sterilization systems.

III. Related Art

Low temperature application of hydrogen peroxide vapor is highly effective when sterilizing objects having relatively open and accessible surfaces such that the hydrogen peroxide vapor can easily surround and contact all surfaces of the object and sterilize these surfaces. To date, low temperature application of hydrogen peroxide vapor has proven to be more difficult when sterilizing objects having diffusion limited interiors and particularly long, narrow lumens. This is because hydrogen peroxide vapor degrades to water and oxygen over time when coming in contact with many materials used to form the surface of such lumens. Thus, the hydrogen peroxide vapor degrades as it diffuses into the interior of the lumen due to the large surface to cross-section ratio of the lumen. Water droplets collecting in the interior of the lumen can block the passage of hydrogen peroxide vapor into the lumen. This degradation limits the diametric size and lengths of lumens that can be sterilized with current vapor-phase hydrogen peroxide systems. There is a need for improved systems and methods to enhance the penetration of vapor sterilants down long narrow objects such as the lumens of tubular devices.

A variety of methods have been employed to sterilize objects having long, narrow lumens, but each of these methods has its shortcomings. Liquid sterilants have been employed in systems commonly referred to as endoscope reprocessors. These systems can combine some of the cleaning and disinfecting steps into a single device. However, the final step is a water rinse which reduces the effectiveness of such systems. Reprocessors are able to provide high level disinfection, but are incapable of sterilizing such objects Dry boosters and wet boosters have been coupled to lumen devices for sterilization purposes. A dry booster is an object with an internal volume that is typically coupled to one end of the lumen of a device before the device is placed in a vacuum chamber. When the lumen and booster are at a vacuum, the sterilant vapor then added to the vacuum chamber passes through the lumen to fill in the void space of the booster. A wet booster is similar to a dry booster in that it is attached to a lumen device to be sterilized before the device is placed in the vacuum chamber. In the case of a wet booster, liquid sterilant is contained in the booster that vaporizes as the vacuum chamber is evacuated. This draws sterilant vapor from the wet booster through the lumen to sterilize the device. Dry and wet boosters are time consuming and clumsy to use. The use of such devices also introduces mated surfaces between the booster and the lumen device which are difficult to sterilize.

Special sterilization trays have also been described in prior art. These trays have a sealable barrier defining two volumes. The tray is also equipped so that a pressure differential can be created between the two volumes. Generally, when these trays are employed the lumen device is placed across the sealable barrier with the two ends of the lumen on opposite sides of the barrier. When sterilant is added to the higher pressure side of the barrier, the pressure differential causes the sterilant to flow through the lumen device toward the lower pressure side of the barrier to sterilize the lumen. Such sterilization trays are also cumbersome to use and introduce mated surfaces between the barrier and tubular wall defining the lumen of the device which are difficult to sterilize.

Various methods to concentrate hydrogen peroxide by removing water have also been described in prior art. Increasing the vapor concentration of hydrogen peroxide outside a lumen provides a greater potential for the hydrogen peroxide to diffuse into a lumen before degrading to low levels. It also reduces the concentration of water vapor, which may prevent hydrogen peroxide from reaching surfaces. The concentration of aqueous hydrogen peroxide that can be shipped by air, however, is limited to about 59% and requires that only small volumes are present in each container. Several methods have been described in prior art to increase the vapor concentration above that of 59% hydrogen peroxide. These are generally methods to remove some of the water vapor with a vacuum pump while retaining much of the hydrogen peroxide. These methods have improved lumen penetration, but at the cost of greater material degradation of the items that are sterilized due to the exposure to highly concentrated hydrogen peroxide vapor.

These prior art methods described above have shortcomings solved by the present invention. The present invention allows full sterilization of the load even when the load includes devices having long, narrow lumens. In addition, the present invention does not employ special devices that must be coupled to the lumen device or special trays of the type described above. Finally, the present invention does not increase the overall concentration of hydrogen peroxide, but rather redistributes the concentration of hydrogen peroxide to the inside of lumens thus maintaining overall material compatibility with the sterilization process.

An object of the present invention is to provide a sterilization system with enhanced sterilant penetration into lumen devices.

Another object of the invention is to provide a sterilization system with a sterilization area variable in size.

Still another object of the invention is to provide a sterilization system having a sterilization area with a movable boundary.

A further object of the invention is to provide a sterilization system with a sterilization area, the size of which can be compressed or expanded in a controlled fashion.

SUMMARY OF THE INVENTION

The present invention provides a sterilization system. More particularly, the sterilization system includes a vacuum chamber having a sterilization area, the size of which may be varied. The sterilization chamber is vacuum-tight and includes a sealable access panel to add and remove items to be sterilized. The varying volume of the sterilization area is achieved by providing a movable boundary or surface. The movable boundary may take the form of a piston, a bellows, a bladder, a diaphragm or a balloon. The motion of the movable boundary can be controlled to produce desired compression and expansion of the sterilization area, both in terms of rate and amount, to enhance the sterilization process. The system includes an inlet valve to allow the sterilization area to vent to atmospheric pressure, an outlet valve placed between the sterilization area and a vacuum pump to allow the sterilization area to be evacuated, and a sterilant inlet valve placed between the sterilization area and a source of sterilant to allow sterilant to be added to the sterilization area. A variety of devices may be employed to move the boundary in a controlled fashion to vary the volume of and therefore the pressure within the sterilization area.

The volume variation induces pressure variations that can be beneficial in at least five ways. First, as the boundary moves to expand the volume of the sterilization chamber, degraded hydrogen peroxide is removed from the interior of the lumen device. Second, as the boundary moves to contract the volume in the sterilization chamber, the higher concentration of hydrogen peroxide vapor outside the lumen device is forced into the lumen. Third, by controlling the rate of expansion and contraction, it is possible to control the type of flow (laminar or turbulent) within the lumen. Laminar flow in a tube has a parabolic velocity profile in the radial direction, while turbulent flow is much more uniform in the radial direction. This difference may be exploited to preferentially move non-degraded hydrogen peroxide farther into the lumen and degraded hydrogen peroxide out of the lumen. Fourth, by injecting hydrogen peroxide into the chamber in an appropriate amount, the contraction of the volume of the chamber will increase the partial pressure of the hydrogen peroxide above its vapor pressure and lead to condensation on surfaces including the inside of the lumen. Within the lumen, the condensed hydrogen peroxide will have a greater concentration than the vapor hydrogen peroxide. Fifth, subsequent expansion of the volume of the chamber will cause the lower concentration vapor in the lumen to be removed and replaced by higher concentration vapor that revaporizes from the liquid condensate. The overall result will be a higher concentration of vapor hydrogen peroxide inside the lumen.

BRIEF DESCRIPTION OF THE DRAWINGS

The foregoing features, objects and advantage of the invention will become apparent to those skilled in the art from the following detailed description of a preferred embodiment, especially when considered in conjunction with the accompanying drawings.

For purposes of clarity and brevity, like elements and components bear the same designations and numbering throughout the figures.

DESCRIPTION OF THE PREFERRED EMBODIMENT

Figure 1:
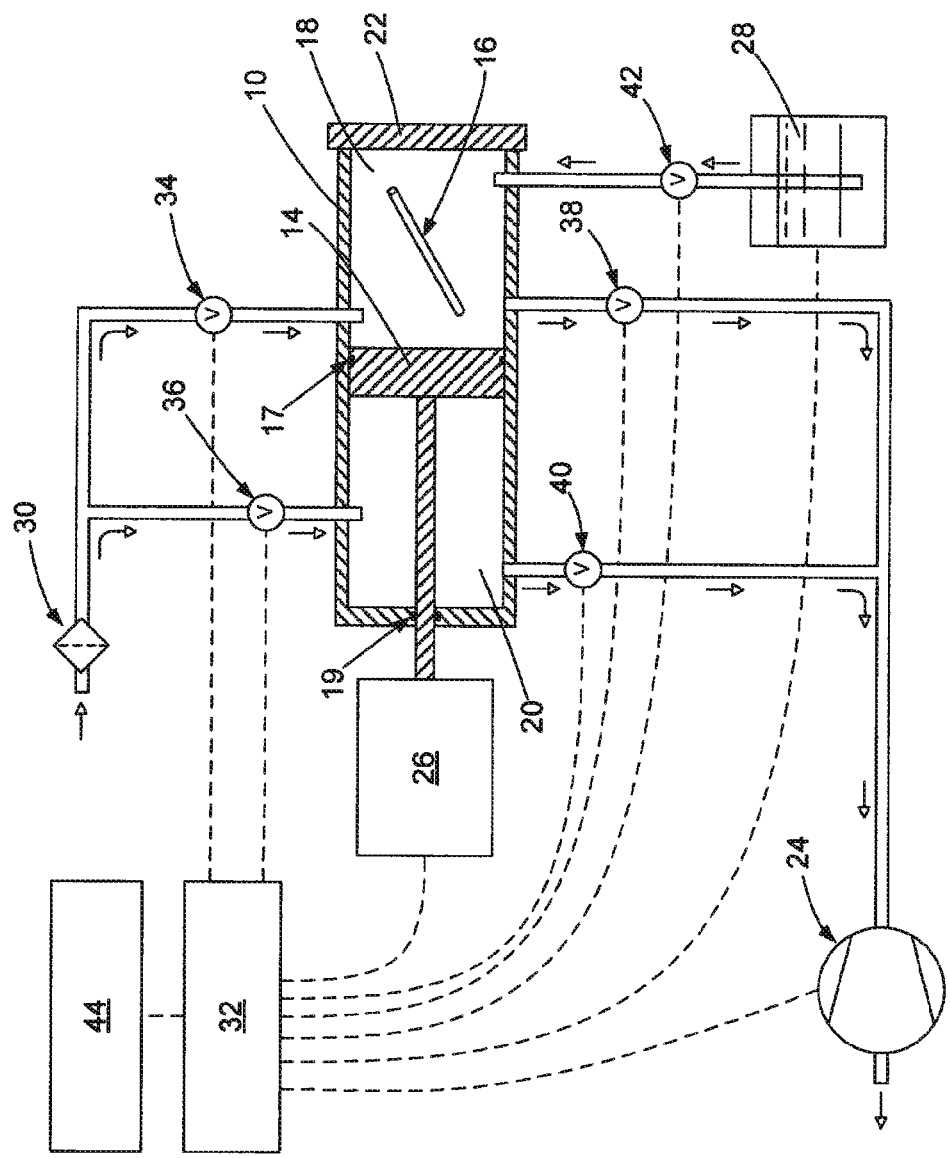
FIG. 1 is a schematic view of a sterilization system having a sterilization chamber comprising a first sterilization area, the size of which is variable.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise. In addition, the terms sterilant gas and sterilant vapor are used interchangeably and refer to the sterilant in a gas phase that may or may not condense on objects depending on the chamber conditions.

FIG. 1 is a schematic diagram of a variable volume sterilizer system constructed in accordance with the present invention. The sterilization chamber 10 contains a first volume or region referred to herein as area 18 into which item(s) 16, including tubular items to be sterilized are placed and into which sterilant is admitted. The first area 18 is in fluid communication with a movable boundary 14, so that the volume of the first area 18 can be changed. More specifically, the size of area 18 can be increased or decreased by moving the movable boundary 14.

Figure 5:
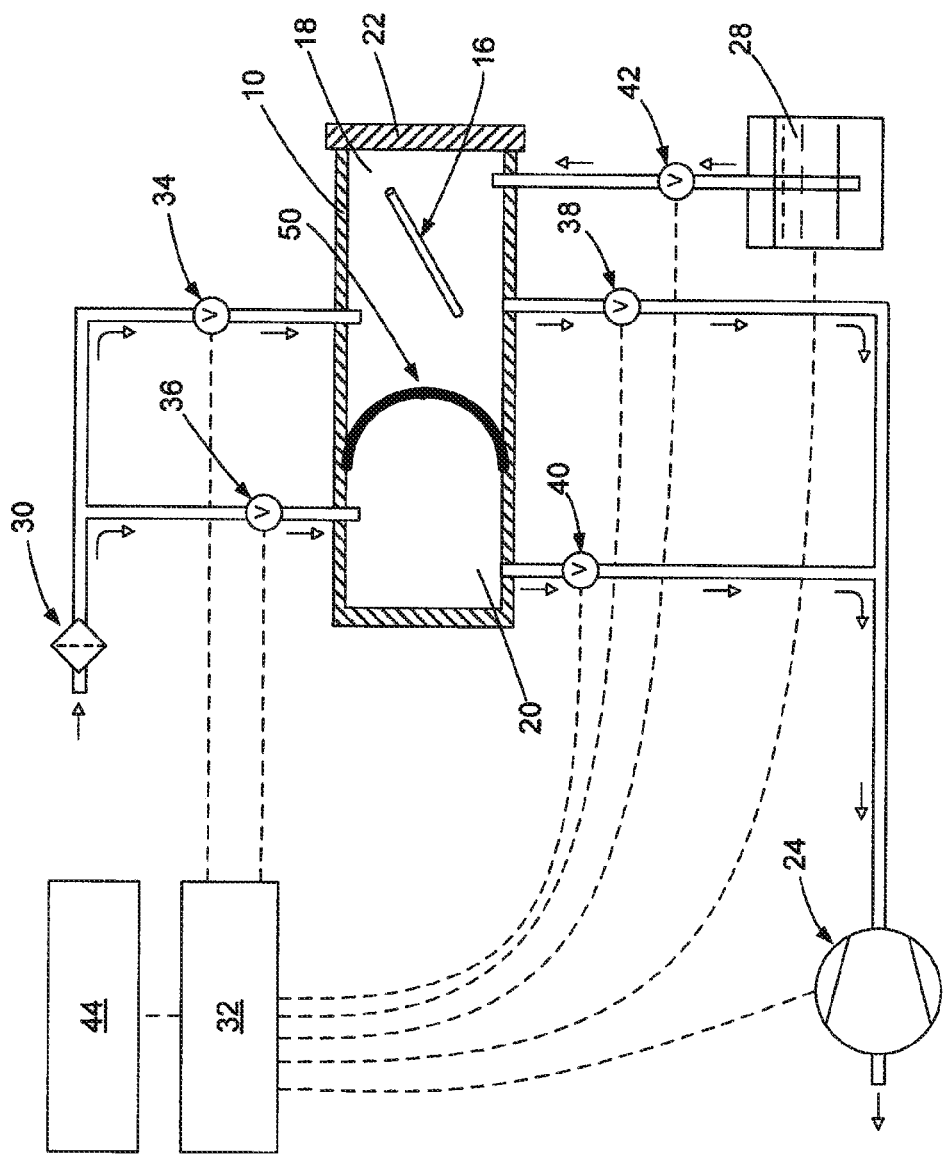
FIG. 5 is a schematic view of a fifth embodiment of a sterilizer with a variable sterilization chamber area.
Figure 6:
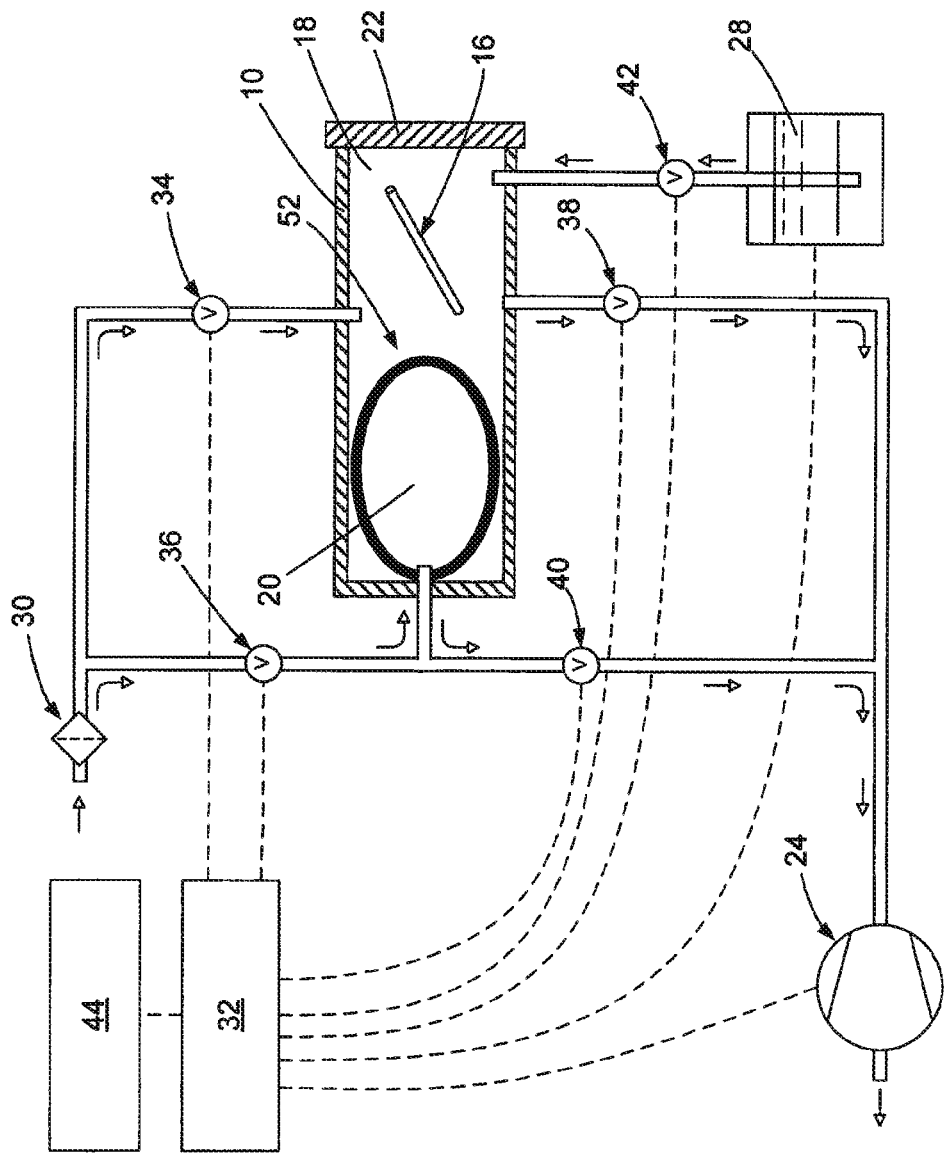
FIG. 6 is a schematic view of a sixth embodiment of a sterilizer with a variable sterilization area.

The position of the movable boundary 14 is varied and controlled during a sterilization cycle. The movable boundary 14 may take many forms including: a piston as shown in FIGS. 1-4, a bellows, a flexible bladder 50 as shown in FIG. 5 or a balloon 52 as shown in FIG. 6. These will be described more fully below. The form of the movable boundary 14 is less important than the principle of changing the size of the first area 18 as a result of changing the position of the movable boundary 14.

With reference again to the embodiment of FIG. 1, the sterilization chamber 10 includes an access panel 22 so that the interior of the first area 18 of the sterilization chamber 10 can be accessed to add or remove item(s) 16 to be sterilized. This may take the form of a door on a hinge, a sliding panel, or any other object which may be displaced to allow access to the interior of area 18 of the sterilization chamber 10, and then replaced and sealed. The exterior of sterilization chamber 10 and the access panel 22 may be made of aluminum, stainless steel, acrylic, polycarbonate or any other material capable of withstanding the loads incurred as a result of lowering the pressure inside the sterilization chamber 10. These materials are either compatible with hydrogen peroxide liquid and vapor, or may be treated with coatings that are compatible with hydrogen peroxide liquid and vapor. Such coatings include Teflon and other fluorocarbons, polyethylene or other compatible materials. The movable boundary 14 (if rigid) may be made of similar materials or treated with similar optional coatings to make the movable boundary 14 compatible with hydrogen peroxide liquid and vapor. An O-ring seal 17 is operatively disposed between the periphery of the movable boundary 14 (a piston in FIG. 1) and the wall of chamber 10 to isolate the chamber area 18 from the chamber area 20 while allowing the movable boundary 14 to slide relative to the interior wall of the chamber 10.

Figure 4:
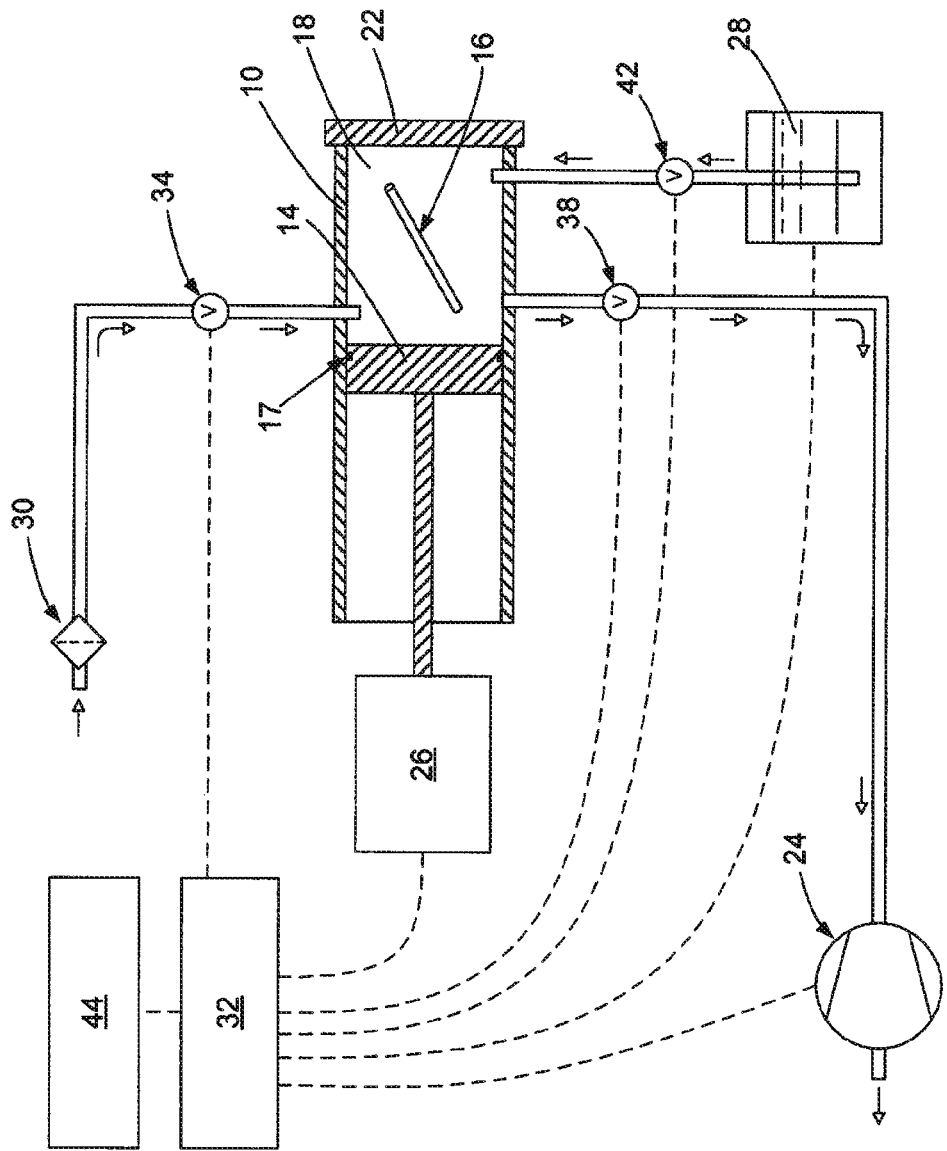
FIG. 4 is a schematic view of a fourth embodiment of a sterilizer with a variable sterilization chamber area.

The systems depicted in the embodiments of FIGS. 1 and 4 include a mechanical actuator 26 to produce controlled motion of the movable boundary 14. The mechanical actuator 26 may take many forms, including solenoid actuators, motor driven stages, pneumatic actuators, hydraulic actuators, or any other actuator capable of controlling movement of the movable boundary 14 with sufficient power. It is preferable to use a mechanical actuator 26 which is capable of controlling the distance, direction and rate at which the movable boundary 14 moves, but simple full-stroke actuators may also be used. As will be explained in other embodiments described below, the movement of the movable boundary 14 can be accomplished without the need for a separate mechanical actuator 26.

The item(s) 16 to be sterilized are represented by a slender tube with a lumen in FIG. 1. The item(s) 16 can be placed directly into chamber 10, but are preferably packaged in cases, containers or wraps (not shown). These packaging methods are commonly used for sterilization processes to maintain sterility of the item(s) when the packages are removed. The item(s) 16 may also be combined with other lumen devices and with non-lumen devices in the packages or chamber.

Evacuation of the sterilization chamber 10, and more specifically area 18 of the chamber, is accomplished using a suitable vacuum source 24 such as a vacuum pump which is connected to area 18 via outlet valve 38. Arrows are shown in the figures to indicate the flow direction when a valve is open and a pressure differential exists across that valve. The vacuum source 24 may be of any type suitable to reduce the pressure in area 18 to the desired level. Preferably, a vacuum pump is capable of reducing the pressure below 1 Torr and most preferably, below 0.4 Torr. The vacuum source 24 is preferably a dry pump so that lubricating oils cannot backflow from the vacuum pump to the sterilization chamber 10.

The outlet valve 38 is depicted generically in FIG. 1. Any type of valve may be used here, including solenoid valves, pneumatic valves, butterfly valves or any other type of valve that can open and close communication between the vacuum source 24 and area 18 of the sterilization chamber 10. The valve type is preferably normally closed, but normally-open or valves with variable opening may also be used.

Venting of area 18 of the sterilization chamber 10 is accomplished by opening a first inlet valve 34 located between area 18 of the sterilization chamber 10 and an inlet air filter 30. While air filter 30 may be eliminated from the design, it is preferable to include an inlet air filter 30 to filter particles in the ambient air that might contaminate the item(s) 16 to be sterilized in the sterilization chamber 10, and to protect the first volume inlet valve 34 from debris. Most preferably, the inlet air filter 30 is a high efficiency particulate air (HEPA) filter.

The first inlet valve 34 shares the characteristics of the first outlet valve 38. The first inlet valve 34 is depicted generically in FIG. 1. The valve is preferably a normally-closed solenoid valve, but other types of valves may be used here, including pneumatic valves, butterfly valves. Also, the valve type need not be normally closed. Normally open or valves with variable opening may also be used. What is important is that the valve 34 can be opened to permit air to enter area 18 and closed to prevent air from entering area 18.

Sterilant is admitted to area 18 of the sterilization chamber 10 by opening a sterilant valve 42 located between area 18 of the sterilization chamber 10 and a sterilant source 28 as shown in FIG. 1. The sterilant valve 42 is preferably a normally-closed solenoid valve. Again, other types of valves may be used here, including pneumatic valves, butterfly valves or any other type of valve or device that can open and close communication between the sterilant source 28 and area 18 of the sterilization chamber 10. The valve type need not be normally-closed. Normally-open or valves with variable opening may also be used. The sterilant valve 42 may be replaced with other devices including pumps to admit sterilant to the sterilization chamber 10. The sterilant source 28 is shown with a reservoir of liquid sterilant. The source 28 may contain liquid, gaseous or liquid sterilant that is vaporized. Preferably, the sterilant is hydrogen peroxide, but other liquid or vapor sterilants could be used with this system and these methods as well.

FIG. 1 also shows a valve 40 positioned between area 20 of the sterilization chamber 10 and the vacuum source 24 as well as a valve 36 between the air filter 30 and the area 20 of the sterilization chamber 10. Together with the o-ring seal 17 and seal 19 these valves are used to control the pressure within area 20 so that, for example, it matches the pressure within area 18 where actual sterilization of items such as 16 is performed. The valves 36 and 40 and the connections between area 20 and the vacuum source 24 and filter 30 are optional. They may also be used instead of a separate mechanical actuator 26 to control the position of the movable boundary 14.

Certain advantages are achieved when both a mechanical actuator 26 and valves 36 and 40 are provided. The valves can be used to evacuate area 20 or otherwise control the pressure within area 20 relative to the pressure within area 18 to alter the force actuator 26 must supply to move the boundary 14. Use of the actuator 26 allows for greater control of the expansion and contraction of area 18 in terms of the size of area 18 the rate of expansion or contraction of area 18 and the frequency of the expansion and contraction cycles employed.

The system shown in FIG. 1 includes a control/power electronics subsystem 32 to provide power and control signals to the vacuum source 24, sterilant source 28, mechanical actuator 26, inlet valve 34, outlet valve 38, the sterilant valve 42, and the valves 36 and 40. A computer 44 is coupled to the control/power electronics subsystem 32 such that the entire sterilization system can be operated under program control via the computer 44. Control in this manner streamlines the operation, improves the function, and allows complex and repeatable sterilization processes to be conducted. The computer 44 may be an external device, a single-board device, or other on-board device, or may be a microprocessor.

Figure 2:
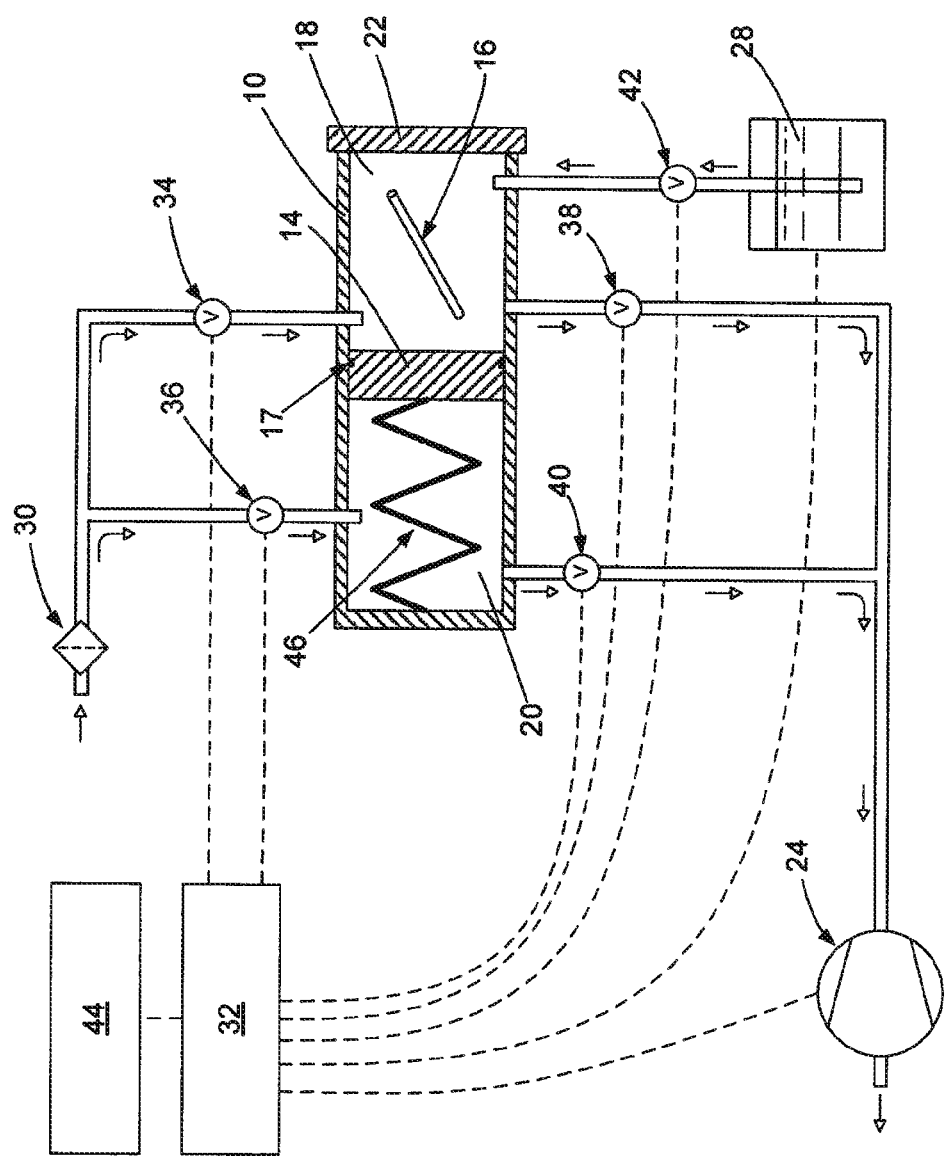
FIG. 2 is a schematic view of a second embodiment of a sterilizer with a variable sterilization area.

FIG. 2 is a schematic diagram of a second embodiment of a variable volume sterilizer system. In this embodiment, as in the embodiment shown in FIG. 1, the sterilization chamber 10 is divided into two portions: a first area 18 in which item(s) to be sterilized 16 are placed and into which sterilant is admitted; and the second area 20. Area 18 and area 20 are separated by a movable boundary 14 that is sealed with respect to the chamber walls, but slidable such that the relative sizes of chamber areas 18 and 20 can be altered as part of the sterilization process via controlled movement of the movable boundary 14. More specifically, the first area 18 and second area 20 are separated by the movable boundary 14, so that when the second volume 20 is increased, the first volume 18 consequently decreases, and vice versa. One advantage of using a second area 20 within the sterilization chamber 10 is that this area may also be evacuated. When the second area 20 is at a pressure near to that of the first area 18, the differential pressure force on the movable boundary 14 is dramatically reduced. This allows a relatively simple and low powered actuation system 26 such as the spring 46 shown in FIG. 2 to be used. For example, if the spring 46 is a compression spring, the spring 46 tends to force the movable boundary 14 rightward in FIG. 2 so that the second area 20 is enlarged. To actuate the movable boundary 14, filtered air inlet valve 36 is closed and vacuum inlet valve 40 is opened to draw a vacuum in the second area 20. This moves the movable boundary 14 against the force of the spring 46 so that the second area 20 is reduced while the first area 18 is increased. Alternatively, and preferably, the spring 46 can be an extension spring. In this case, the barrier 14 is biased to the left in FIG. 2 such that the second area 20 is initially relatively small. Opening the filtered air inlet valve 36 when the first area 18 is at low pressure will cause the movable boundary 14 to shift rightward and increase the volume of the second area 20. Many types of springs could be used in a similar manner. Other devices may also be used to produce a force on the movable boundary 14 in a similar fashion.

By way of example and with reference to FIG. 2, the pressure in area 20 can be drawn down by opening valve 40 and closing valve 36 with pump comprising vacuum source 24 running. At the same time, pressure in area 18 can be drawn down by closing air inlet valve 34 and sterilant inlet valve 42 and opening valve 38. The spring 46 will then displace the movable boundary 14 leftward to reduce the volume of area 20 and increase the volume of area 18. The several valves can then all be closed to maintain a steady state before opening valve 42 to admit sterilant into area 18. Valve 42 can be left open just long enough to permit the pressure in area 18 to increase so as to reach a first desired level. Valve 42 can then be closed so that area 18 is sealed. The valves 36 and 40 can then be actuated to overcome the spring force of spring 46 and move the movable boundary 14 to the right in FIG. 2 to decrease the volume of area 18 thereby increasing the pressure in area 18 without changing the amount of fluid in area 18. During the sterilization cycle, the movable boundary 14 can be reciprocally moved back and forth in a controlled manner to change the pressure in area 18 without changing the quantity of fluid within area 18 by actuating the valves 36 and 40 to changes the pressure within area 20. Changing the pressure in area 18 in this fashion will cause the sterilant to move into and out of the lumens of devices such as 16 to be sterilized.

Certain advantages are achieved when both a mechanical actuator and valving, such as valves 36 and 40, are provided as shown in FIGS. 1 and 2. The valves can be employed to evacuate area 20 or otherwise control the pressure of area 20 relative to the pressure of the area 18 to alter the force actuator 26 must supply to move boundary 14 or resist movement of boundary 14. Use of the actuator 26 allows for greater control of the expansion and contraction of area 18 in terms of the changes in volume of area 18, the rate of expansion or contraction of area 18 and the frequency of the expansion and contraction of area 18. As discussed below with reference to FIGS. 3 and 4, systems having only such valves or only such an actuator may be employed without deviating from the invention.

Figure 3:
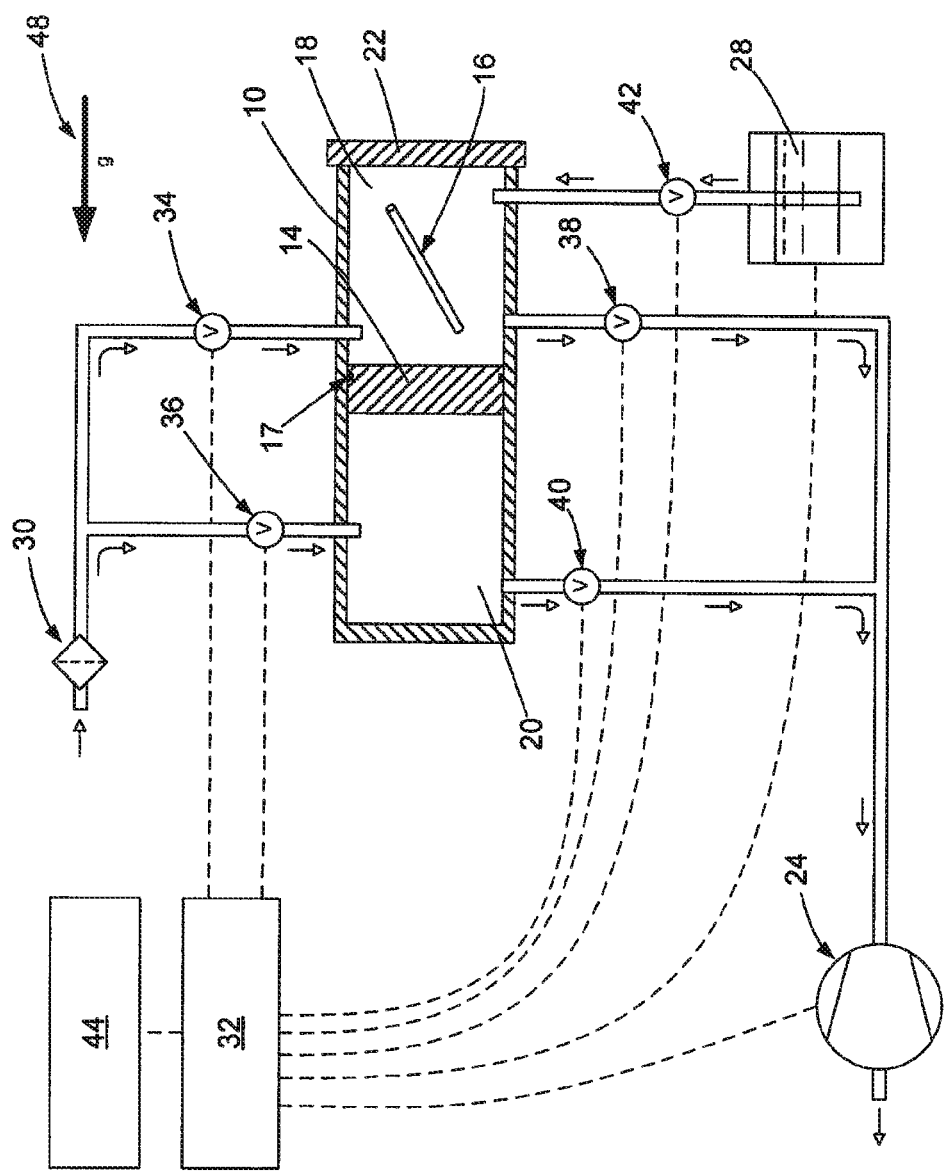
FIG. 3 is a schematic view of a third embodiment of a sterilizer with a variable sterilization chamber area.

FIG. 3 is a schematic diagram of a third embodiment of a variable volume sterilizer system similar to the embodiment of FIG. 2. In this embodiment, the spring 46 has been removed and the movable boundary 14 is moved by using the controlled actuation of inlet valve 36 and/or the outlet valve 40. Any pressure differential between areas 18 and 20 will cause the movable boundary 14 to move. When the pressure in area 20 is lower than the pressure in area 18, the boundary will move to reduce the volume of area 20 and expand the volume of area 18 in an effort to equalize the pressures of the two areas. Likewise, when the pressure in area 20 is greater than the pressure in area 18, the movable boundary 14 will move in the opposite direction. Arrow 48 in FIG. 3 is present to suggest that gravity can also be employed to expand the size of area 18 except when the pressure in area 20 is sufficiently higher than the pressure in area 18 to resist the force of gravity.

FIG. 4 is a schematic diagram of a fourth embodiment of a variable volume sterilizer system. In this embodiment valves 36 and 40 of the previously described embodiments have been eliminated such that actuator 26 exclusively controls the position of the movable boundary 14.

FIG. 5 is a schematic diagram of a fifth embodiment of a variable volume sterilizer system. In this embodiment, the movable boundary 14 is a flexible diaphragm 50 rather than the piston or a rigid member of the type shown in FIGS. 1-4. The volume of the second area 20 is varied by changing the pressure in the second area 20 to the left of the diaphragm relative to the pressure in the first area 18. This is achieved in a fashion similar to that described above via actuation and control of the valves 36 and 40 with respect to area 20 and valves 34, 42 and 38 with respect to area 18. If the pressure in area 20 is higher than the pressure in area 18, the diaphragm will bulge rightward as shown in FIG. 4 and reduce the volume of area 18 thereby causing the pressure in area 18 to increase without additional fluid being admitted into area 18. Likewise, if the pressure in area 20 is less than the pressure in area 18, the diaphragm will bulge toward the left into area 20 thereby reducing the pressure in area 18 without withdrawing any fluid from area 18. Changes in the pressure differential between areas 18 and 20 can be used to promote the flow of sterilant within the lumens of devices such as 16 to be sterilized.

FIG. 6 is a schematic diagram of a sixth embodiment of a variable volume sterilizer system. In this embodiment, the movable boundary 14 is the surface of a balloon 52 contained within the sterilization chamber 10. The volume 20 occupied by the balloon 52 can be expanded or contracted by varying the pressure inside the balloon relative to the pressure outside the balloon 52. This is again achieved through operation of the valves 34, 42 and 38 relative to the area 18 outside of the balloon 52 and the valves 36 and 40 relative to the area inside of the balloon. For example, the balloon 52 can be fully deflated by closing valve 36 and opening valve 40. A vacuum can be drawn in area 18 exterior to balloon 52 by closing valves 34 and 42 and opening valve 38. Valve 38 can then be closed and valve 42 opened to admit a desired quantity of sterilant into area 18. Then valve 40 can be closed and valve 36 opened to inflate the balloon causing the volume of area 18 to shrink as the balloon inflates. This will cause a pressure increase in area 18 even though no additional fluid has been admitted into area 18. The balloon 52 can be cyclicly inflated and deflated during the sterilization process through controlled actuation of valves 36 and 40 to literally pump sterilant into and out of the lumens of the items 16 to be sterilized.

Figure 7:
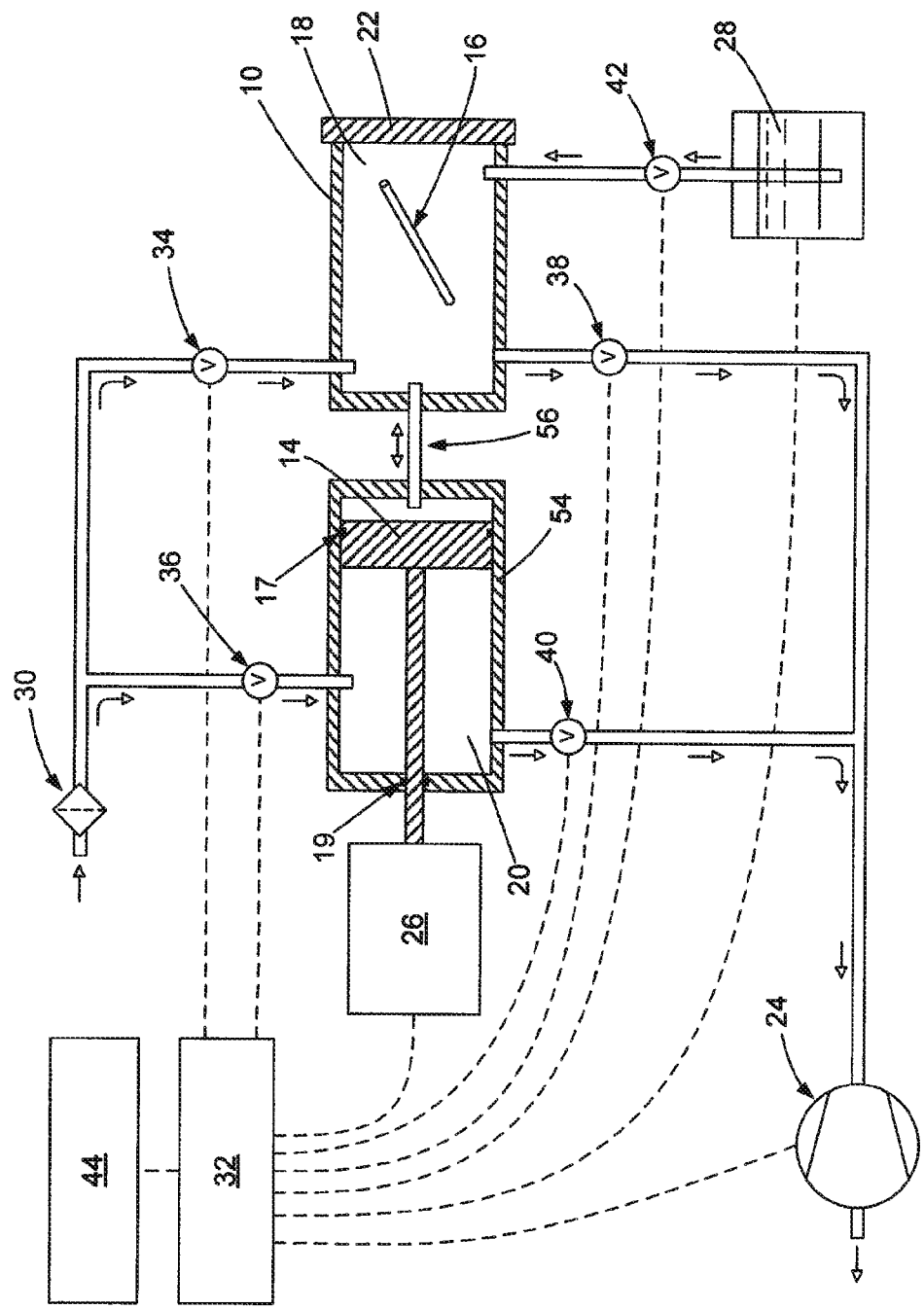
FIG. 7 is a schematic view of the seventh embodiment thereof.

Referring next to FIG. 7, it shows a further embodiment of the present invention similar in most respects to the embodiment of FIG. 1, save for the fact that the sterilization chamber 10 does not itself contain the movable boundary member 14. Instead, a separate cylinder 54 is coupled by a fluid flow path 56 to the interior of the sterilization chamber 10 and the movable boundary 14 is slidably disposed within the cylinder 54.

Those skilled in the art will appreciate that when the movable boundary 14 is moved leftward in FIG. 7 by the actuator 26, it will create a negative pressure within the sterilization chamber 10 and, likewise, when the movable boundary is shifted to the right, an increased pressure results in the sterilization chamber 10.

In the embodiment of FIG. 7, the actuator 26 can be dispensed with and the movable boundary 14 may be displaced by controlling the pressure in the cylinder 20 relative to that in the chamber 10. For example, by opening the valve 40 leading to the vacuum pump with the vent valve 36 closed, the movable barrier 14 will move to the left in FIG. 7 thereby reducing the pressure in the chamber 10. Subsequently, by closing the outlet valve 40 and opening the vent valve 36, the movable barrier 14 will be shifted rightward, thereby increasing the pressure within the sterilization chamber 10. This operation is similar to that described in connection with the earlier embodiment of FIG. 3.

The following method of sterilization may be employed using any of the embodiments described above or any other embodiment incorporating the invention. First, item(s) 16 to be sterilized, that may or may not have an open ended tubular lumen, are placed into area 18 of the sterilization chamber 10 through the access panel 22. The access panel 22 is then closed. Next, the first area 18 is evacuated by a suitable vacuum source and the movable boundary 14 is positioned to maximize the size of area 18. When the first area 18 reaches a desired vacuum level of approximately 0.4 Torr, all of the valves are made to close. The sterilant valve 42 is then opened to allow vaporized sterilant into the sterilization chamber 10 to admit a desired quantity of sterilant into area 18. This raises the pressure in area 18 to, for example, approximately 10 Torr. The sterilant valve 42 is then closed again, sealing area 18 of the sterilization chamber 10.

Next, steps are taken to compress the volume of first area 18 to a smaller size and thus increase the pressure in the first area without admitting additional fluid into the first area 18. This is achieved by increasing the volume of the second area 20 using any suitable mechanism for doing so (those described above just being some examples). Typically, the volume of area 18 will be half or less of its original volume after these steps are taken. The pressure rises in chamber area 18 due to this compression and results in the sterilant being forced into the item(s) 16 to be sterilized. This is particularly useful for lumen devices and other devices with diffusion restricted spaces. The sterilant gas flows under pressure into the lumens rather than simply diffusing into the lumens.

A holding period is then permitted to transpire. During the holding period, the relative sizes of the first area 18 and the second area 20 may be held constant. Alternatively, during this holding period the size of the second area 20 may be repeatedly reduced and expanded in a controlled manner without admitting any additional fluid into the first area 18 to modulate the pressure in the first area 18. After the holding period, the first volume outlet valve 38 is opened to evacuate sterilant vapor from the sterilization chamber 10. The evacuation continues until the pressure reaches about 0.4 Torr, at which time the outlet valve 38 is closed and the inlet valve 34 is opened. The first area 18 is vented to atmospheric pressure, the movable boundary 14 is returned to its starting position and the item(s) to be sterilized 16 can be removed by opening the access panel 22. Of course, steps outlined above can be repeated one or more times before removing the items 16 to ensure complete sterilization. Other modifications may be made to the sterilization cycle described above without deviating from the invention.

An important advantage of the present invention is that quick compression in the first area 18 forces sterilant vapor into lumen passages before the sterilant vapor can condense on surfaces due to the increased partial pressure of the sterilant gas. In addition, quick compression raises the vapor temperature as well as the pressure. On subsequent expansion of the first area 18, any condensed sterilant may revaporize. Repeated compression and expansion processes can also propagate sterilant farther and farther into lumen devices by controlling the frequency and rate of the compression and expansion steps. The compression and expansion steps need not be equal or constant in speed or period. The process of compression and expansion may also be supplemented in an overall sterilization process to include additional sterilant injections, venting steps and evacuation steps.

Other modifications to the embodiments described above are possible. These include: using both the first area 18 and second area 20 for sterilization rather than just the first area 18; using additional areas beyond area 20 to control the size of the first area 18; applying this method to other gas/vapor sterilization methods beyond hydrogen peroxide systems; and applying this method to gas plasma sterilization systems to help move plasma species into and out of devices and packaging.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method of low temperature, sterilizing of an object comprising:
    (a) inserting the object into the first area of a sterilization chamber;
    (b) reducing the pressure of the first area to a predefined level;
    (c) injecting a quantity of a sterilant vapor consisting of hydrogen peroxide into the first area;
    (d) reducing the volume of the first area while the first area remains sealed to increase the pressure in the first area inducing the sterilant vapor consisting of hydrogen peroxide to flow over the object;
    (e) venting the first area to atmospheric pressure; and
    (f) removing the object from the sterilization chamber.

2. The method of claim 1 and further including the steps of:
    (g) after step (d), increasing the volume of the first area while the first area remains sealed to decrease the pressure in the first area; and
    (h) repeating the steps (d) and (g) a predetermined number of times prior to steps (e) and (f) to create fluid motion within the chamber whereby sterilant vapor movement with respect to the object is enhanced.

3. A method of sterilizing an object comprising:
    (a) providing sterilization apparatus comprising (i) a sterilization chamber having a first area whose volume is defined at least in part by a movable boundary, the first area having an access panel, (ii) a first inlet valve for venting the first area and a first outlet valve coupled to a vacuum source for evacuating the first area, (iii) a vapor sterilant consisting of hydrogen peroxide source coupled to the first area by a sterilant valve, and (iv) means for moving the boundary to expand and contract the effective volume of the first area;
    (b) inserting a load to be sterilized in the first area through the access panel;
    (c) closing the first inlet valve and opening the first outlet valve with the vacuum source operational to evacuate the first area;
    (d) subsequently opening the sterilant valve when the pressure in the first area reaches a predetermined low value to admit a vapor sterilant consisting of hydrogen peroxide, into the first area; and (e) cyclicly displacing the movable boundary to vary the pressure up and down within the first area and thereby induce movement of the vapor sterilant with respect to the load.

4. The method of claim 3 and further including after step (e) the step of:
   (f) drawing a vacuum in the first area to remove residual sterilant; and
   (g) opening the first inlet valve to vent the first area to atmospheric pressure.

5. A method for low temperature, sterilizing objects some of which include a lumen comprising the steps of:
   (a) providing sterilization apparatus comprising (i) a sterilization chamber having a first area whose volume is defined at least in part by a movable boundary, a second area separated from the first area by the movable boundary, the first area having an access panel, (ii) a first inlet valve for venting the first area and a first outlet valve coupled to a vacuum source for evacuating the first area, (iii) a vapor sterilant consisting of hydrogen peroxide source coupled to the first area by a sterilant valve, and (iv) means for moving the boundary to expand and contract the effective volume of the first area;
   (b) inserting objects, some of which include a lumen, in the first area of the sterilization chamber via said access panel and subsequently reclosing and sealing the access panel;
   (c) displacing the movable boundary to maximize a volume of the first area;
   (d) evacuating the first area to a predetermined low pressure with the vacuum source;
   (e) closing the first input valve and the first output valve and opening the sterilant valve to admit a desired quantity of vapor sterilant consisting of hydrogen peroxide into the first area until the pressure in the first area reaches a predetermined higher pressure;
   (f) closing the sterilant valve;
   (g) displacing the movable boundary in a direction to reduce the volume of the first area and increase the pressure therein to thereby drive the vapor or sterilant consisting of hydrogen peroxide through lumens of the objects;
   (h) maintaining the increased pressure for a predetermined holding period;
   (i) drawing a vacuum in the first area to remove residual sterilant therefrom;
   (j) opening the first input valve to vent the first area to atmospheric pressure; and
   (k) removing the sterilized objects from the sterilization chamber via the access panel.

6. The method of claim 5 wherein the pressure in the first area is repeatedly raised and lowered by cyclicly displacing the movable boundary during step (h).

7. The method of claim 5 wherein step (g) is achieved by increasing the volume of the second area.

8. A method for low temperature, sterilizing of tubular objects comprising the steps of:
   (a) providing sterilization apparatus comprising (i) a sterilization chamber haying a first area whose volume is defined, at least in part, by an elastic expansible balloon disposed within the sterilization chamber, the first area having an access panel, (ii) a first inlet valve for venting the first area and a first outlet valve coupled to a vacuum source for evacuating the first area, (iii) a source of sterilant vapor consisting of hydrogen peroxide coupled to the first area by a sterilant valve, and (iv) means for inflating and deflating the elastic expansible balloon to expand and contract the effective volume of the first area;
   (b) inserting the tubular objects to be sterilized in the first area of the sterilization chamber via said access panel and subsequently reclosing and sealing the access panel;
   (c) deflating the balloon to a predetermined volume to thereby maximize the volume of the first area;
   (d) evacuating the first area to a predetermined low pressure with the pump;
   (e) closing the first input valve and first output valve and open the sterilant valve to admit a desired quantity of vapor sterilant consisting of hydrogen peroxide into the first area;
   (f) closing the sterilant valve;
   (g) driving the sterilant vapor consisting of hydrogen peroxide over and through the tubular object by inflating the balloon to reduce the volume of the first area and increase the pressure therein;
   (h) maintaining the increased pressure for a predetermined holding period;
   (i) drawing a vacuum in the first area to remove residual sterilant vapor consisting of hydrogen peroxide therefrom; and
   (j) opening the first input valve to vent the first area.

9. . The method of claim 8 wherein the balloon is cyclicly deflated and inflated during the holding period to induce movement of the sterilant vapor consisting of hydrogen peroxide with respect to the objects.

* * * * *